(12) United States Patent
Furner et al.

(10) Patent No.: US 8,920,734 B2
(45) Date of Patent: Dec. 30, 2014

(54) CANDLE DISPENSER DEVICE

(75) Inventors: Paul E. Furner, Racine, WI (US);
Phillip Kongshaug, Racine, WI (US);
Donald J. Schumacher, Racine, WI (US); Jeffrey P. Mills, Barrington, IL (US)

(73) Assignee: S.C. Johnson & Son, Inc., Racine, WI (US)

( * ) Notice: Subject to any disclaimer, the term of this patent is extended or adjusted under 35 U.S.C. 154(b) by 260 days.

(21) Appl. No.: 13/540,665

(22) Filed: Jul. 3, 2012

(65) Prior Publication Data

US 2014/0010715 A1    Jan. 9, 2014

(51) Int. Cl.
*A61L 9/03*    (2006.01)

(52) U.S. Cl.
USPC .......................................... 422/125; 424/409

(58) Field of Classification Search
CPC ........................................................ A61L 9/03
USPC .......................................... 422/125; 424/409
See application file for complete search history.

(56) References Cited

U.S. PATENT DOCUMENTS

| | | | |
|---|---|---|---|
| 1,243,439 A | | 10/1917 | Myers |
| 2,742,342 A | | 4/1956 | Dew et al. |
| 3,279,118 A | | 10/1966 | Allen |
| 3,605,437 A | * | 9/1971 | Litton ............................ 63/1.15 |
| 4,224,017 A | | 9/1980 | Kayne |
| 4,781,895 A | | 11/1988 | Spector |
| 5,840,246 A | | 11/1998 | Hammons et al. |
| 6,309,986 B1 | | 10/2001 | Flashinski et al. |
| 6,337,080 B1 | | 1/2002 | Fryan et al. |
| 6,365,169 B1 | * | 4/2002 | Rosenblatt ..................... 424/404 |
| 6,482,365 B1 | | 11/2002 | Soller |
| 6,503,459 B1 | | 1/2003 | Leonard et al. |
| 6,780,382 B2 | | 8/2004 | Furner et al. |
| 7,138,130 B2 | | 11/2006 | Davis et al. |
| 7,413,435 B2 | * | 8/2008 | Jameson et al. .............. 431/292 |
| 7,622,073 B2 | * | 11/2009 | Schramm et al. ................. 422/5 |
| D627,088 S | | 11/2010 | Schwartz et al. |
| 7,883,677 B2 | | 2/2011 | Palozzi |
| 8,047,837 B2 | | 11/2011 | Furner et al. |
| 2006/0057526 A1 | | 3/2006 | Kubicek et al. |
| 2006/0147338 A1 | | 7/2006 | Nakatsu et al. |

(Continued)

FOREIGN PATENT DOCUMENTS

| | | |
|---|---|---|
| EP | 1310264 A1 | 5/2003 |
| EP | 1825748 A2 | 8/2007 |

(Continued)

OTHER PUBLICATIONS

PCT/US2013/049043 International Search Report and Written Opinion dated Feb. 11, 2014.

(Continued)

*Primary Examiner* — Sean E Conley

(57) ABSTRACT

Devices dispense air treatment chemicals in response to heat generated by a candle. There is a support mounted on the candle that carries a substrate bearing the air treatment chemical. The support holds a heating plate with substrate thereon over the candle, and a chimney in the heating plate (and passage through the substrate) allow heated air to pass through when the candle wax is being combusted. Heat dispersal fins are formed along the chimney. A washer shaped substrate is provided that is made of fiberglass bound with polyvinyl alcohol and bears the air treatment chemical.

19 Claims, 5 Drawing Sheets

(56) References Cited

U.S. PATENT DOCUMENTS

2007/0194144 A1* 8/2007 Davis et al. .................... 239/34
2011/0139894 A1   6/2011 Masterson et al.
2012/0093491 A1   4/2012 Browder et al.

FOREIGN PATENT DOCUMENTS

| WO | WO 99/51912     | 10/1999 |
| WO | WO 2005/058031  | 6/2005  |
| WO | WO 2006/031669  | 3/2006  |
| WO | 2009005723 A1   | 1/2009  |

OTHER PUBLICATIONS

A page of a Jun. 5, 2012 web site by Sabic entitled "Valox Resin", admitted prior art.

Two pages of a Jun. 20, 2011 web site by Soycandles.com entitled Febreze Home Collection Soy Candles by Procter and Gamble, admitted prior art.

* cited by examiner

CANDLE DISPENSER DEVICE

CROSS-REFERENCE TO RELATED APPLICATIONS

Not applicable

STATEMENT REGARDING FEDERALLY SPONSORED RESEARCH/DEVELOPMENT

Not applicable

BACKGROUND OF THE INVENTION

The present invention relates to devices that dispense air treatment chemicals from a substrate mounted above a candle flame. More particularly, the invention relates to structures associated with such devices for rendering them more suitable for controlling flying insects outdoors.

A variety of devices are known for dispensing volatilizable air treatment chemicals such as pest control materials (e.g., insecticides, insect repellants, or insect growth control regulators), air scents or deodorizers (e.g. masks), allergen control ingredients, disinfectants, sanitizers or other materials. In some of these devices the air treatment chemical is mixed with candle wax and is dispensed during a candle burning process (where the chemical is released primarily from the heated wax surrounding the wick). While this is a common technique for dispensing a variety of fragrances, and even some materials such as citronella that have some insect control capability, typically it has been less successful when dispensing certain particularly desirable pest control materials.

There have been attempts to improve efficiency by placing some structures over the candle. However, most of these devices were focused on improving candle burning efficiency in a deep-cup type candle, rather than distributing air treatment chemicals from sources other than the wax.

Other attempts have been made to use the heat from a candle (or other heat source) to distribute air treatment chemicals from an adjacent impregnated pad or the like. See e.g. U.S. Pat. Nos. 2,742,342, 4,781,895, 6,482,365, 6,503,459, and 7,138,130. However, these devices required relatively expensive constructions to achieve their results, or suffered inefficiencies, or were not be optimally suited for use outdoors.

One particularly desirable type of candle dispenser was disclosed in U.S. Pat. No. 8,047,837. There, a candle heated a chimney form of heating plate that was supported over the candle. A washer shaped impregnated substrate was positioned on the plate around the chimney and dispensed active when heated air passed through the chimney, warmed the plate, and thereby warm the substrate. However, the dispensing characteristics of this candle were not optimally controlled.

Thus, a need continues to exist for improved candle dispenser assemblies, particularly where the dispenser is primarily intended for outdoor use.

BRIEF SUMMARY OF THE INVENTION

In one aspect the invention provides a device for dispensing an air treatment chemical. The device includes a housing (e.g. a dish or a cup) for retaining a candle, a platform (e.g. a legged platform such as a tripod) positionable adjacent (e.g. mounted on) the housing, the platform having at least one air entry passageway between adjacent portions of the platform (and a top of the housing), a heating plate supported on the platform so as to extend over the candle (the heating plate having a chimney), and a substrate positioned on the heating plate around the chimney (the substrate bearing a volatile air treatment chemical). The substrate has a top plan view area of greater than 13 square centimeters (preferably greater than 17 square centimeters; most preferably between 18 and 20 square centimeters).

Preferably there is a mesh/screen positioned over the substrate, the candle has wax and a wick, the chimney is positioned over the wick, and both the substrate and mesh are essentially washer shaped in plan view. The mesh can frictionally abut against a portion of the heating plate to help trap the substrate against the heating plate.

Particularly when the size of the substrate grows larger it is very desirable to have a fin structure is positioned along the chimney which extends radially inwardly into an air shaft of the chimney to dispense heat from the chimney radially along the heating plate. This can include opposed fins from opposite sides of the chimney.

In another preferred form the platform is a tripod, the housing is in a form of a dish, a bottom of the dish rests on a base that is separable from the dish, and the base is suitable to be repositioned over the substrate to retard volatilization of the air treatment chemical from the substrate between uses of the candle. In one form the base has a radially extending grip tab to facilitate such repositioning.

In some embodiments the platform is mounted on the dish, the dish interfits with the platform by a snap fit connection, and the heating plate interfits with the platform by a bayonet connection. In these embodiments the air treatment chemical is selected from the group consisting of volatile insect control agents (e.g. metofluthrin mosquito repellent), fragrances, disinfectants, sanitizers, and deodorizers.

In another form a dish portion of the device is weighted at a lower portion so as to cause the dish portion to automatically move to a more upright position if the dish portion is tipped over sideways. There may also be an outlet vent provided between a lower side of the heating plate and a radially outward upper side of the platform.

For highly preferred embodiments the candle is positioned relative to the heating plate so as to be suitable to cause a portion of the heating plate to operate at a temperature of between 54 degrees C. and 176 degrees C. when the candle is lit (e.g. between 80 and 105 degrees C.).

In another aspect the invention provides a substrate which comprises fiberglass bound with polyvinyl alcohol and an insect control ingredient, and the platform is made from polybutylene terephtalate. Polybutylene terephtalate and other similar plastics, resist catching fire. However, if the candle catches fire more broadly than at the wick for an extended period of time, this type of platform material has a melting point that is sufficiently low to permit the platform to melt into the candle (and thereby snuff it automatically).

In some embodiments (not shown) there can be a peel-off seal abutting on inner and outer rings of the heating plate to help retard volatilization from the substrate before the device is used.

It should be appreciated that various embodiments of the present invention have a variety of advantages. Surprisingly, very large area substrates necessary for outdoor insect control can be heated in a relatively uniform manner by a candle. This provides efficient dispensing, as well as typical candle advantages (e.g. light).

Yet, various embodiments help prevent unintended human contact with the substrate, or premature disassembly of the parts. Still other embodiments help minimize unwanted volatization of active when insects are not being controlled (e.g. when the product is on a store shelf). Still other embodiments help portions of the device to move towards a self-righted position, and/or more reliably coordinate the burning time of the candle with the use-up time of the substrate.

Still other embodiments have wide legs that reduce the likelihood that ambient wind will snuff the candle. Nevertheless, gaps between the legs permit the candle to be lit while the dish and platform are still assembled together, and facilitate proper air flow. This also allows the candle to function as an aesthetically pleasing light source.

Moreover, the components of the assembly are relatively inexpensive to produce, and are intuitive for a consumer to use.

The foregoing and other advantages of the present invention will be apparent from the following description of the preferred embodiments. As these embodiments are merely illustrative, they are not intended to represent the full scope of the invention. Thus, reference should therefore be made to the claims herein for interpreting the scope of the invention.

DETAILED DESCRIPTION OF THE PREFERRED EMBODIMENTS

Figure 1:
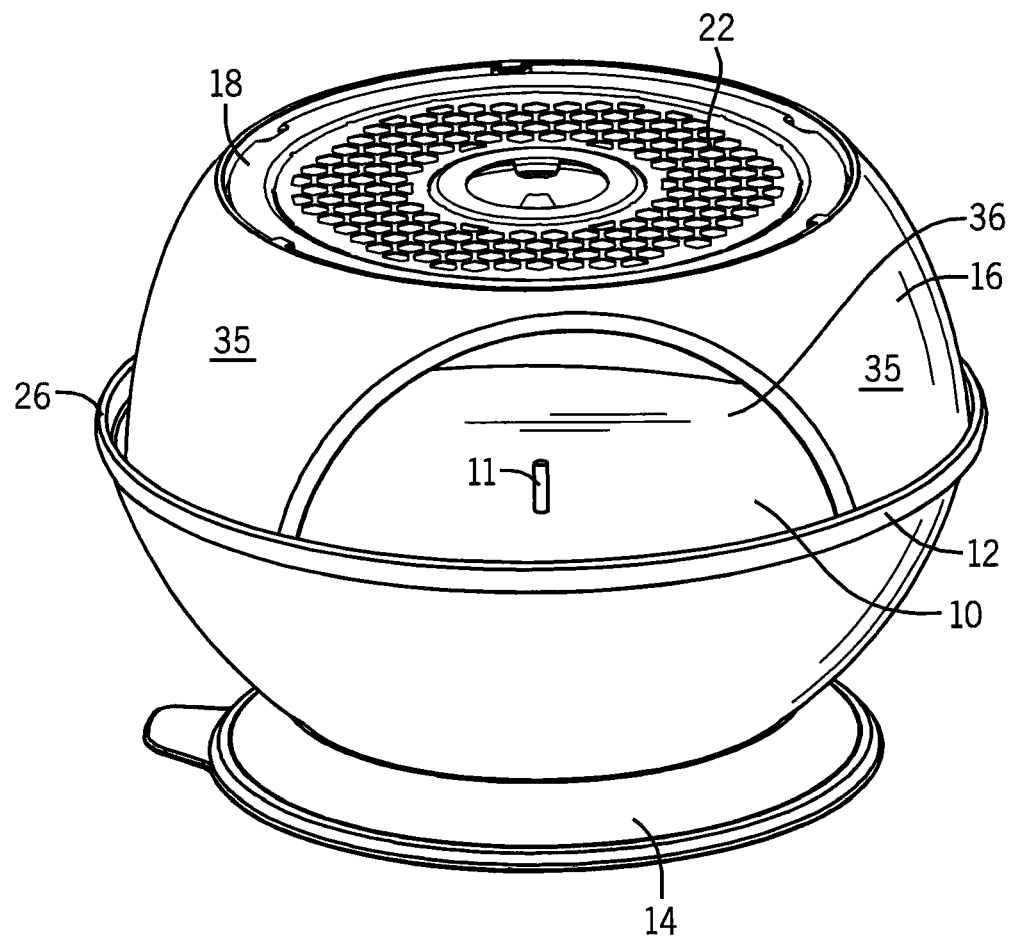
FIG. 1 is an assembled perspective view of a preferred candle dispenser device of the present invention.

A preferred device for dispensing an air treatment chemical is shown in FIGS. 1-5. It has a wax candle 10 with a wick 11, a dish shaped housing 12 retaining the candle, a combined base/lid 14, a tripod shaped support/platform 16, a heating plate 18, a substrate 20 that has applied to it a volatile active (e.g. metofluthrin in a solvent), and a metal mesh washer-shaped screen 22 on top of the substrate.

The candle 10 can be made of a conventional candle wax. Optionally, a fragrance or other secondary air treatment chemical (e.g. citronella) may be mixed in with the wax.

The housing 12 may be made of a tin plated steel (or other heat resistant material), and have an upper lip/bead 26 immediately over an internal groove 27. The housing 12 may be sufficiently heavy near its bottom (e.g. due to placement of the wax or extra metal near its bottom) to tend to move towards a self-righted position if it is tipped on its side.

Figure 2:
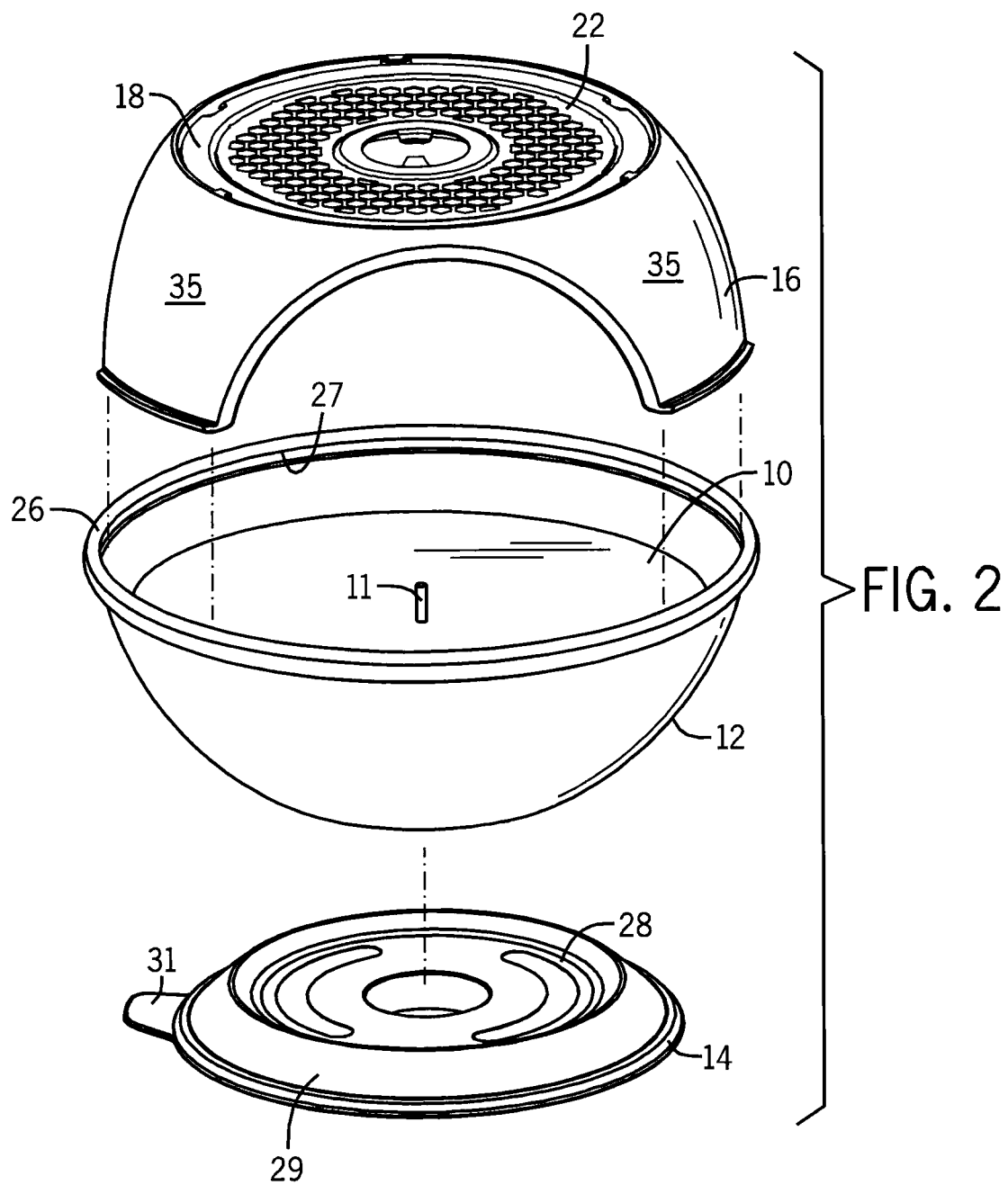
FIG. 2 is a partially exploded perspective view thereof.

As best seen in FIG. 2, the base/lid 14 has an internal receiving cavity 28, a central through opening 29 and a grip tab 31. The base/lid 14 may support the bottom of the housing 12 up off a picnic table or the like when the base/lid is positioned as shown in FIG. 1. This is the preferred position when the device is being used for controlling insects.

Figure 5:
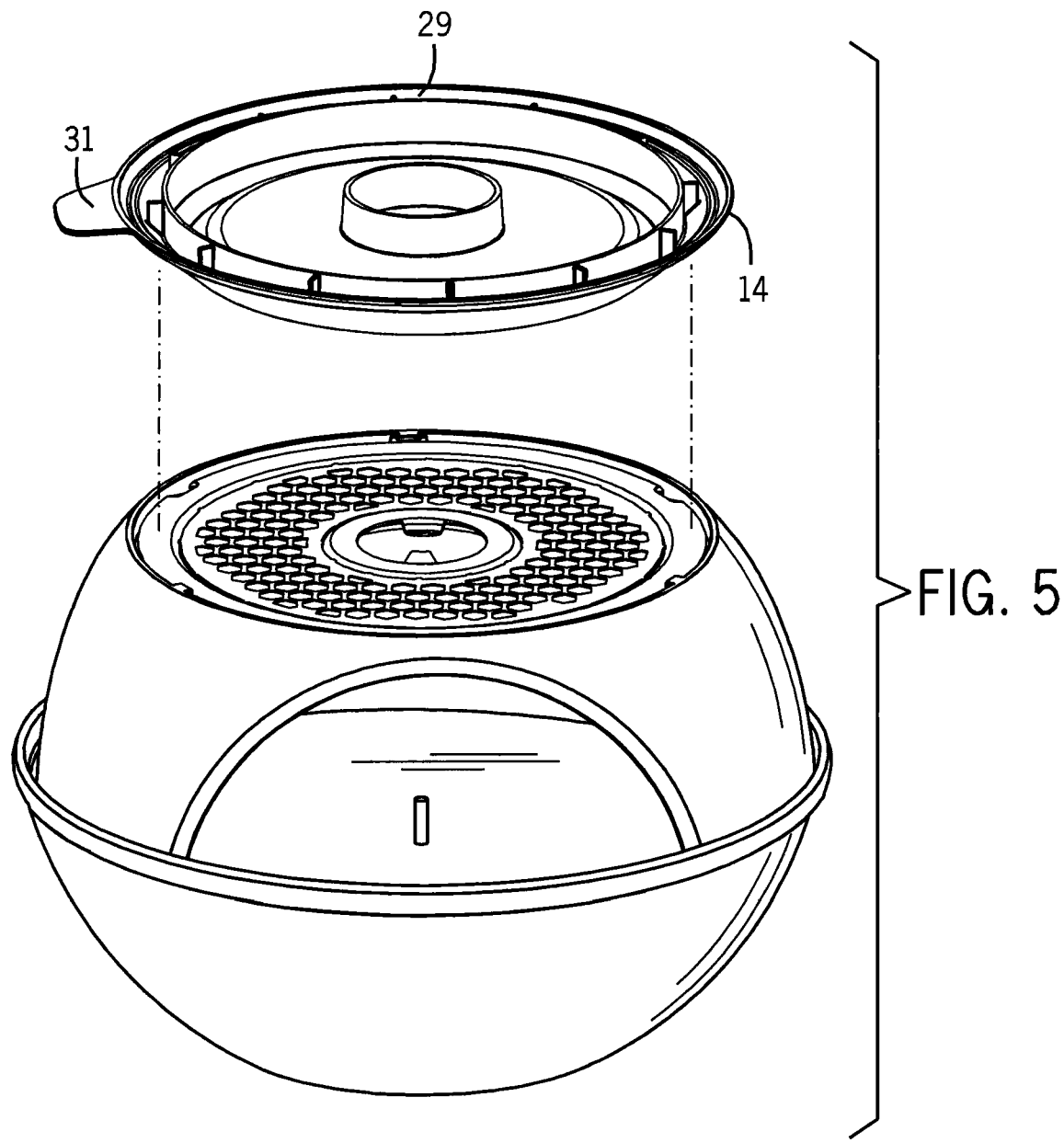
FIG. 5 is a view similar to FIG. 1, but with the base repositioned to be about to be used as a lid.

However, as indicated by FIG. 5, the base/lid 14 may alternatively be removed from below the housing 12 and positioned over, and then on the subassembly 70, as a cover. This is the preferred position when the device has not yet been purchased by the consumer, or between uses. When used as such a cover (in the FIG. 2 orientation) the opening 29 will still allow any residual candle heat to vent off, but still seal against the top of chimney 32 and outer flange 33 of heating plate 18 to isolate the substrate 20.

The tripod support/platform 16 has three wide legs 35, each of which has a radially outwardly projecting foot that can flex snap into groove 27 when the housing 12 and platform 16 are pushed together (as shown in FIG. 1). This results in the creation of arc shaped openings 36 between the legs 35 that provide air vent paths to feed air to the candle and also allow candle flicker light to be seen from outside the candle (so as to light a patio at night in an aesthetically pleasing manner). These openings are small enough so that most wind gusts will be blocked by legs 35 before snuffing the candle prematurely, yet large enough so that a human hand can insert a match through one to light the candle (without disassembling the device).

If desired, one can form the platform/support 16 of a thermoplastic that will not readily catch fire, and has a melting point above normal candle operating temperatures, but has a melting point below a temperature that might occur if a candle pool of wax were to catch fire apart from the wick (e.g. a vandal squirts charcoal lighter fluid on an operating candle). This melting attribute has the advantage of causing the tripod to melt into the candle and automatically snuff it in such a circumstance. An example of a suitable material for this purpose is Valox® polybutylene terephtalate.

Figure 3:
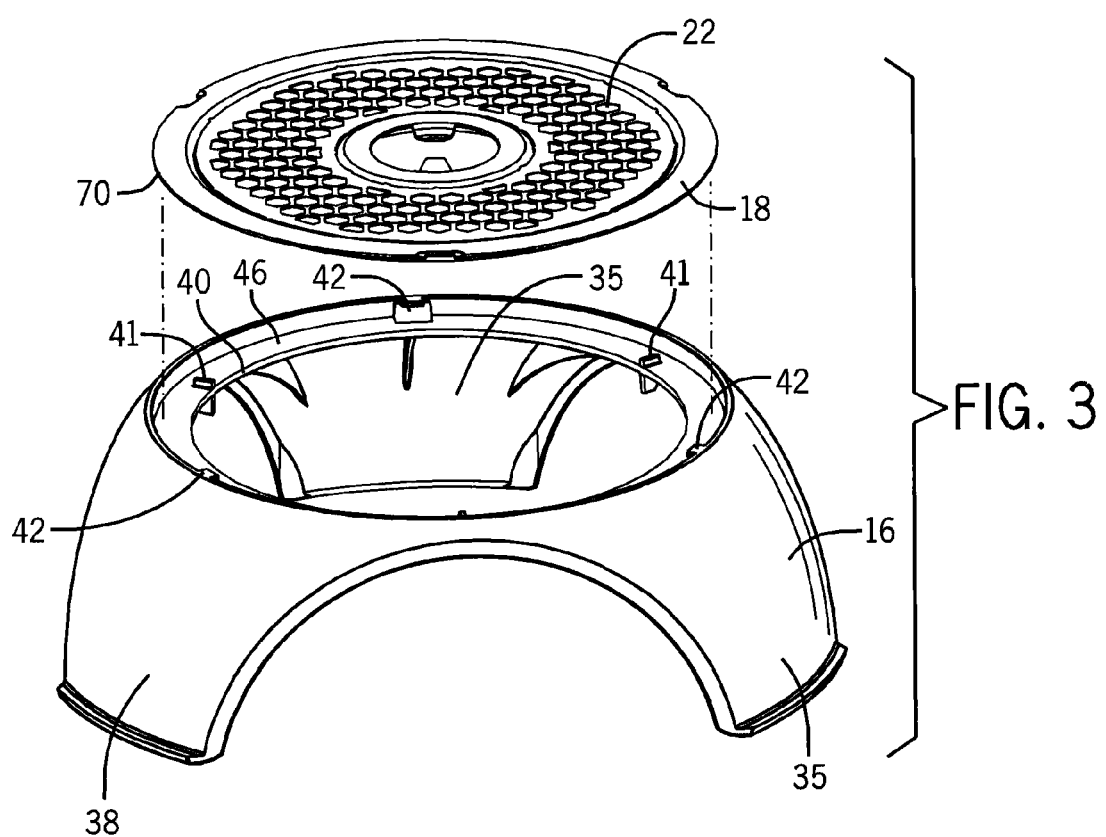
FIG. 3 is a further exploded perspective view of an upper portion of the FIG. 2 device.
Figure 4:
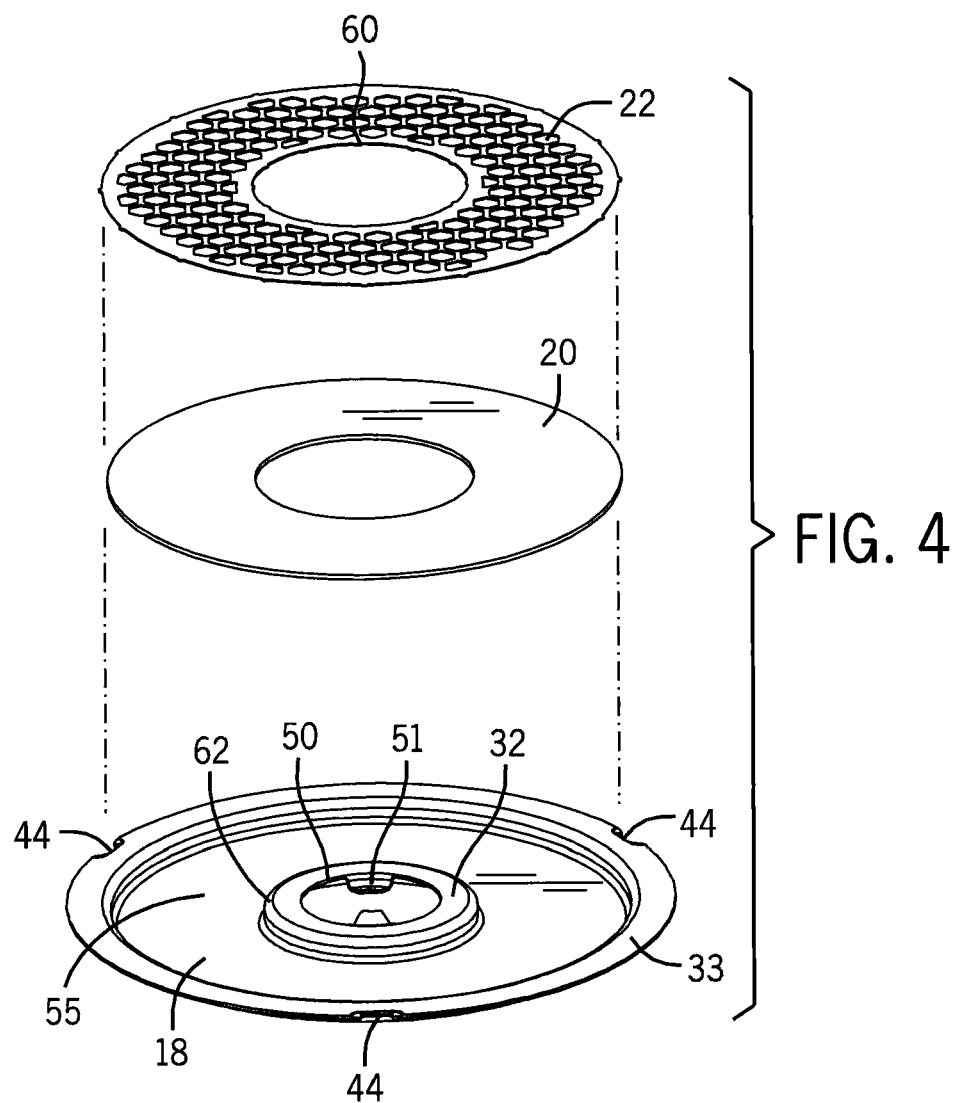
FIG. 4 is a still further exploded perspective view of an upper subassembly of the FIG. 3 components.

As best seen in FIG. 3, there is an upper ledge 40 near the top of the tripod. The ledge has three stand-offs 41 and three catches 42.

Heating plate 18 is preferably made of aluminum or another material that is heat resistant and readily transfers heat. In a preferred form it has three attachment notches 44 (see FIG. 4) on its outer radius. The notches 44 can be aligned over catches 42 so that the subassembly 70 can be dropped onto stand-offs 41. The subassembly can then be rotated to cause catches 42 to be over a portion of the subassembly other than the notches 44, thereby catching the subassembly 70 in a bayonet type connection.

Because flange 33 is held up off the ledge 46 of the tripod by the stand-offs 41, there is an air outlet passageway between the ledge 46 and flange 33. Heated air from the candle can therefore be driven in part past an outer edge of the subassembly 70, thereby applying heat to an outer radial portion of the heating plate 18.

Centrally located on the heating plate 18 is an air shaft 50 of chimney 32. Heat dispersal fins 51 extend radially inwardly into the shaft so as to "catch" and dispense the heat from heated air passing in the air shaft 50.

Because the heating plate 18 is heated along its radially inward edge, along its radially outward edge, and also from the bottom, the heat plate tends to warm up essentially uniformly adjacent the substrate. This creates a much more efficient heating pattern.

To achieve reasonable outdoor insect control one preferably wants to use a relatively large substrate and screen (e.g. greater than 13 square cm; preferably about 19 square cm). Designing for essentially uniform radial heating is particularly important, and a difficult design problem, with such a large screen.

In its most preferred form the substrate 20 is washer-shaped and fits compactly into a corresponding recess 55 of the heating plate 18. The substrate is preferably made of a porous heat resistant material such as fiberglass bound with polyvinyl alcohol (e.g. a Craneglas® material). This material is preferred because in addition to being heat resistant it surprisingly tends to retard a highly volatile active such as metofluthrin from flashing off prematurely, while still allowing effective insect control. One could instead use other substrates such as a ceramic or sand/resin based substrate if a less volatile active is used.

Air treatment chemicals may be presented in a wide variety of formulations. See e.g. U.S. Pat. Nos. 6,309,986 and 6,337,080 for disclosure of a variety of insect control materials, deodorizers, fragrances, sanitizers, and disinfectants known to be suitable for use with heating dispensers. For example, suitable active materials may include (when the volatile material is an insecticide and/or insect repellent), organic phosphorous insecticides, lipidamide insecticides, natural repellents as citronella oil, natural pyrethrins and pyrethrum extract, and synthetic pyrethroids. Suitable alternative synthetic pyrethroids are acrinathrin, allethrin as D-allethrin, Pynamin, benfluthrin, bifenthrin, bioallethrin as Pynamin Forte, S-bioallethrin, esbiothrin, esbiol, bisoresmethrin, cycloprothrin, cyhalothrin, lambda-cyhalothrin, cyphenothrin, empenthrin, esfenvalerate, fenpropathrin, fenvalerate, flucythrinate, taufluvalinate, kadethrin, phenothrin, prallethrin as Etoc, resmethrin, tefluthrin, tetramethrin, or transfluthrin.

When the active is applied to the substrate it may be coated on or impregnated in various ways. For example, the active can be mixed into a hydrocarbon or other solvent, and drops of the mix can be released above the substrate. An air blower can disperse the drops into a mist just as the liquid is about to hit the substrate.

The mesh/screen 22 may be made of a metal such as steel. It serves multiple purposes. Its inner edge 60 may be tightly fit around a portion of the chimney 32 such that tiny barbs on its radial periphery catch onto the heating plate 18 as the screen is pushed into its well. This serves to trap the substrate in place. It also inhibits unintended contact with the substrate 20. Further, the screen helps spread heat more uniformly across the substrate.

The subassembly 70 is suitable to be sold as a refill, such as where the candle is designed for a longer useful life than the substrate 20. For example, the candle could be designed for about sixty hours of use and be sold in a kit with three subassemblies 70 (that are each designed for about twenty hours of use). In such a kit a color change or other use-up cue could be associated with the substrate 20 so that a consumer knows when to replace it. Alternatively, the substrate could be designed to be used up just as the candle is being used up.

In some applications it is desired that the candle be positioned at a height relative to the heating plate so that the majority of the heating plate lower surface inward of flange 33 operates at a temperature of between 54 and 176 degrees C. during the majority of dispensing.

In operation, the wick 11 of the candle 10 is lit with a match or the like, causing the air around the wick to heat up. The warmed air travels upward through the chimney 32 and also out the air pathway between the bottom of flange 33 and tripod flange 46. This causes the heating plate 18 to warm up essentially uniformly, thereby heating the substrate 20 essentially uniformly. This efficiently drives insecticidal active (e.g. metofluthrin) out into the ambient air to control insects such as mosquitoes.

The subassembly 70 is intended to be sold in packaging designed to inhibit release of active before use. One possibility is a tear open pouch enclosing that subassembly. Another possibility is a peel off cover which isolates the substrate from the atmosphere until it is peeled off.

While the above describes preferred embodiments, it should be appreciated that other embodiments are also within the scope of the invention. For example, mosquitoes can be controlled with other actives besides metofluthrin (e.g. transfluthrin), the support may have more or less legs than three, portions of the assembly may be rectangular rather than cylindrical, etc. Regardless, the invention is not to be limited to just the specific embodiments shown or described, and the following claims should therefore be looked to in order to judge the full scope of the invention.

INDUSTRIAL APPLICABILITY

Disclosed herein are improved candle dispenser devices, and substrates for use therewith, such as those bearing insect control agents capable of controlling mosquitoes outdoors.

All documents cited in this patent are, in relevant part, incorporated herein by reference. The citation of any document is not to be construed as an admission that it is prior art with respect to the present invention.

What is claimed is:

1. A device for dispensing an air treatment chemical, the device comprising:
    a housing for retaining a candle;
    a platform positionable adjacent the housing, the platform having at least one air entry passageway between adjacent portions of the platform;
    a heating plate supported on the platform so as to extend over the candle, the heating plate having a chimney; and
    a substrate positioned on the heating plate around the chimney, the substrate bearing a volatile air treatment chemical;
    wherein a bottom of the housing rests on a base that is separable from the housing, and the base is suitable to be repositioned over the substrate to retard volatilization of the air treatment chemical from the substrate between uses of the candle; and
    wherein the base has a hole suitable to permit heat from the candle to be dissipated from the device after the candle has been used, even while the base has been so repositioned over the substrate in a position that retards volatilization of the air treatment chemical from the substrate.

2. The device of claim 1, wherein the substrate has a top plan view area of greater than 13 square centimeters.

3. The device of claim 2, wherein the substrate has a top plan view area of between 18 and 20 square centimeters.

4. The device of claim 1, further comprising a mesh positioned over the substrate.

5. The device of claim 4, wherein the candle has wax and a wick, the chimney is positioned over the wick, and both the substrate and mesh are essentially washer shaped in plan view.

6. The device of claim 5, wherein the mesh frictionally abuts against a portion of the heating plate to help trap the substrate against the heating plate.

7. The device of claim 1, wherein a fin structure is positioned along the chimney which extends radially inwardly into an air shaft of the chimney to dispense heat from the chimney radially along the heating plate and then into the hole of the base.

8. The device of claim 1, wherein the platform is a tripod.

9. The device of claim 1, wherein the housing is in a form of a dish.

10. The device of claim 9, wherein the base has a radially extending grip tab and the hole is centrally located.

11. The device of claim 9, wherein the platform is mounted on the dish and the dish interfits with the platform by a snap fit connection.

12. The device of claim 9, wherein the heating plate interfits with the platform by a bayonet connection.

13. The device of claim 1, wherein the air treatment chemical is selected from the group consisting of volatile insect control agents, fragrances, disinfectants, sanitizers, and deodorizers.

14. The device of claim 1, wherein a dish portion of the device is weighted at a lower portion so as to cause the dish portion to automatically move to a more upright position if the dish portion is tipped over sideways.

15. The device of claim 1, wherein there is an outlet vent provided between a lower side of the heating plate and a radially outward upper side of the platform.

16. The device of claim 1, wherein the candle is positioned relative to the heating plate so as to be suitable to cause a portion of the heating plate to operate at a temperature of between 54 degrees C. and 176 degrees C. when the candle is lit.

17. The device of claim 1, wherein the substrate comprises fiberglass bound with polyvinyl alcohol and an insect control ingredient.

18. The device of claim 1, wherein the platform is made from polybutylene terephtalate.

19. The substrate of claim 1, wherein the substrate is essentially washer-shaped.

\* \* \* \* \*